United States Patent [19]

McCall et al.

[11] 4,032,559
[45] June 28, 1977

[54] N,2-DICYANOACETIMIDATES

[75] Inventors: John M. McCall; Joseph J. Ursprung, both of Kalamazoo, Mich.

[73] Assignee: The Upjohn Company, Kalamazoo, Mich.

[22] Filed: July 28, 1975

[21] Appl. No.: 599,912

[52] U.S. Cl. .................. 260/465.5 R; 260/239 R; 260/239 A; 260/239 B; 260/247.5 R; 260/268 SY; 260/268 CN; 260/293.65; 260/293.87; 260/326.85; 260/464; 260/465 E
[51] Int. Cl.² .................................. C07D 121/16
[58] Field of Search ............. 260/247.5 R, 268 SY, 260/268 CN, 293.87, 465.5 R, 551 C, 464, 468 E

[56] References Cited

UNITED STATES PATENTS

| | | | |
|---|---|---|---|
| 3,068,274 | 12/1962 | McCall | 260/465.5 |
| 3,225,077 | 12/1965 | Schaefer et al. | 260/453 R |
| 3,291,827 | 12/1966 | Huffman et al. | 260/551 |
| 3,641,103 | 2/1972 | Scanlon et al. | 260/465.4 |
| 3,910,928 | 10/1975 | McCall et al. | 260/293.51 |
| 3,948,915 | 4/1976 | Hirayama et al. | 260/256.4 C |

FOREIGN PATENTS OR APPLICATIONS 49-80021  8/1974  Japan

OTHER PUBLICATIONS

Huffman et al., J. Org. Chem., 1963, vol. 28, pp. 1816–1821.
Lwowski, Synthesis, 1971 (5) p. 263.
Hirayama et al., Heterocycles, 1974, vol. 2, No. 4, pp. 457–460.

*Primary Examiner*—Natalie Trousof
*Attorney, Agent, or Firm*—Martin B. Barancik

[57] ABSTRACT

A process for preparing a 2-$R_3$-3-(cyanoimino)-3-(amino)propionitrile which comprises a. reacting a mineral acid addition salt of a 2-cyanoacetimidate of the formula

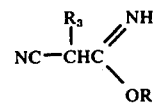

with cyanamide in an organic solvent to form a N,2-dicyanoacetimidate b. reacting a N,2-dicyanoacetimidate of the formula

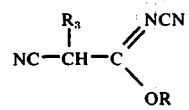

with an amine of the formula

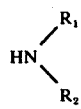

to form a 2-$R_3$-3-(cyanoimino)propionitrile of the formula

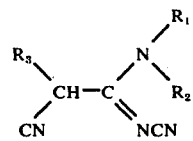

N,2-dicyanoacetimidate compounds are claimed as well.

3 Claims, No Drawings

N,2-DICYANOACETIMIDATES

BACKGROUND OF THE INVENTION

Triamino pyrimidine N-oxides are known in the art. U.S. Pat. No. 3,461,461 specifically discloses and claims certain 6-amino-4-(substituted amino)-1,2-dihydro-1-hydroxy-2-iminopyrimidines. These compounds have various utilities, according to U.S. Pat. No. 3,461,461 such as forming salts with mothproofing agents, aiding in the formation of pickling inhibitors, and pharmaceutical uses, particularly antihypertensive effects.

A new method of preparing the compounds of U.S. Pat. No. 3,461,461 is disclosed in U.S. Ser. No. 464,476, filed Apr. 26, 1974, now U.S. Pat. No. 3,910,928. This method involves the preparation of a novel 2-$R_3$-3-(cyanoimino)-3-(amino)propionitrile of the formula

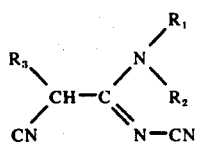

This 3-(cyanoimino)propionitrile is reacted with a hydroxylamine salt and base thereby forming the 6-amino-5-optionally-substituted-2,4-diaminopyrimidine-3-oxide of the formula

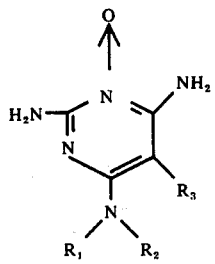

$R_1$, $R_2$, and $R_3$ having the same values as in Ser. No. 464,476, now U.S. Pat. No. 3,910,928.

The necessary disclosure for the preparation of the compounds of formulas I and II from Ser. No. 464,476, now U.S. Pat. No. 3,910,928, is incorporated within this disclosure by reference.

A new method has been devised for synthesizing the 3-(cyanoimino)propionitrile of Formula I. This method involves the preparation of a N,2-dicyanoacetimidate as per the methods of Hirayama, et al., *Heterocycles*, 2, 461 (1974) and Japanese Patent Application J49080-021 of Daichi Seiyaku Company, followed by nucleophilic substitution to prepare the 3-(cyanoimino)propionitrile of Formula I.

BRIEF DESCRIPTION OF THE INVENTION

In accordance with this invention is a new process for preparing a 3-(cyanoimino)propionitrile which comprises a. reacting a mineral acid addition salt of a 2-cyanoacetimidate of the formula

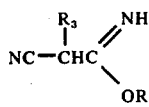

with cyanamide in a organic solvent to form a N,2-dicyanoacetimidate b. reacting a N,2-dicyanoacetimidate of the formula

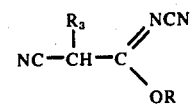

with an amine of the formula

to form a 3-(cyanoimino)propionitrile of the formula

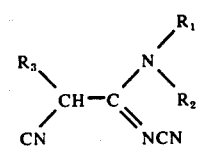

wherein in the above formulas R is selected from the group consisting of alkyl of one to six carbon atoms, inclusive, cycloalkyl of five to seven carbon atoms, inclusive;

$R_1$ and $R_2$ are the same or different and are selected from the group consisting of hydrogen, alkyl of one to eight carbon atoms, inclusive, alkenyl of two to eight carbon atoms, inclusive, cycloalkyl of five to eight carbon atoms, inclusive, unsubstituted or substituted with one to three alkyl groups, said alkyl having from one to three carbon atoms, inclusive, alkyl being the same or different if two or three alkyl groups, and phenylalkyl with alkyl of one to six carbon atoms, inclusive, and $R_1$ and $R_2$, when taken together with the nitrogen atom to which they are attached form a heterocyclic ring of three to seven carbon atoms, morpholino, piperazino, and N-alkylpiperazino, where alkyl is from one to three carbon atoms, inclusive, each of the rings having attached as substituents on carbon atoms thereof zero to three alkyl groups, inclusive, said alkyl being the same or different, if two or more alkyl group substituents, and having from one to three carbon atoms, inclusive;

$R_3$ is selected from the group consisting of hydrogen, alkyl of one to six carbon atoms, inclusive, alkenyl of two to six carbon atoms, inclusive, cycloalkyl of five to eight carbon atoms, substituted or unsubstituted with one to three alkyl groups, said alkyl group having from one to three carbon atoms, inclusive, alkyl being the same or different if two or three alkyl groups, and phenylalkyl wherein alkyl is from one to six carbon atoms, inclusive.

A further aspect of the invention is the conversion of the 2-cyanoacetimidate of Formula III to the N,2-dicyanoacetimidate of Formula IV and the conversion of the latter to the 3-(cyanoimino)propionitrile.

Further aspects of the invention are the N,2-dicyanoacetimidate compounds.

DETAILED DESCRIPTION OF THE INVENTION

The starting materials and compounds prepared by the process of this invention can also exist in tautomeric forms.

Formulas III and IIIa, below, show the tautomeric forms of the 2-cyanoacetimidate.

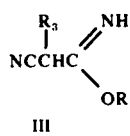   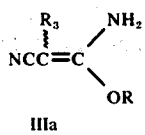

III                    IIIa

Formulas IV and IVa, below, show the tautomeric forms of the N,2-dicyanoacetimidate.

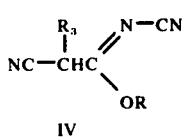   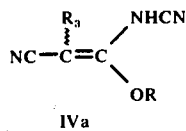

IV                     IVa

Formulas I and Ia, below, show the tautomeric form of the 3-(cyanoimino)-3-(amino)propionitrile

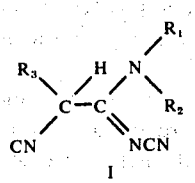   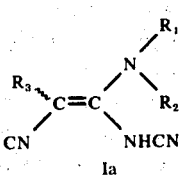

I                      Ia

For convenience, the compounds will be referred to hereafter only in their imino form, not in their "a" form. However, it is to be understood that the compounds prepared by the process of this invention are likely to be mixtures of tautomeric forms, the compositions of which are dependent on such factors as the nature of R, $R_1$, $R_2$ and $R_3$ and the environment. In some instances one form or another may predominate.

As used throughout the specification and in the claims, the phrase "alkyl of one to eight carbon atoms, inclusive" means methyl, ethyl, propyl, butyl, pentyl, hexyl, heptyl, octyl and isomers thereof. A lower carbon atom limitation will have the same scoping, but with that particular number of carbon atoms, in the group, e.g., six, three. The phrase "alkenyl of two to eight carbon atoms, inclusive" means ethylene, propylene, butylene, pentylene, hexylene, heptylene, octylene and isomers thereof. By "isomers thereof," is meant isomers of the hydrocarbon and different positions of the double bond. "Cycloalkyl of five to eight carbon atoms, inclusive," are cyclopentyl, cyclohexyl, cycloheptyl and cyclooctyl.

Examples of alkyl substituted cycloalkyl are 3-methylcyclopentyl, 2,4-diethylcyclohexyl, 2-methyl-4-propylcycloheptyl, 5-isopropylcyclooctyl, 2,4-dimethyl-5ethylcyclohexyl, and 5,5-dimethylcyclohexyl. Phenylalkyl with alkyl of one to six carbon atoms, inclusive, are benzyl, phenylethyl, phenylpropyl, phenylbutyl, phenylpentyl, phenylhexyl and isomers thereof. By "isomers thereof" is meant isomers of the alkyl function and various positions of the phenyl on the alkyl.

The term "mineral acid" denotes an acid of sufficient strength to drive the reaction of the 2-cyanoacetimidate with cyanamide to completion.

Examples of mineral acids include hydrochloric, hydrobromic, sulfuric, and phosphoric.

The $R_3$-substituted 2-cyanoacetimidate mineral acid addition salt starting material of this process can be conveniently prepared by known processes. For example, an appropriately $R_3$-substituted malononitrile, Formula V,

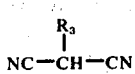

V is reacted with the alcohol ROH wherein R is defined as above, in an organic solvent containing a mineral acid. It is preferred that the reagents involved in this reaction be essentially dry and inert with respect to the reactants to maximize yield. Dryness is preferred. Examples of suitable organic solvents are aryl solvents such as benzene, toluene, xylenes, halogenated lower-alkanes such as methylene chloride, ethylene dichloride, isopropyl chloride, ethers such as diethyl ether, tetrahydrofuran, 1,4-dioxane, and the like. The reaction is conveniently carried out at temperatures of from about 0° to about 100° C., preferably at temperatures of from about 0° to about 40° C.

The $R_3$-substituted malononitrile material is easily prepared by the alkylation of malononitrile.

Compounds illustrative of III are the following:

TABLE I

| R | $R_3$ |
|---|---|
| $CH_3$ | H |
| $C_3H_7$ | $CH_3$ |
| i-$C_5H_{11}$ | cyclohexyl |
| $C_2H_5$ | $C_2H_5$ |
| i-$C_4H_9$ | cyclopentyl |
| $C_6H_{13}$ | 4-methylcyclohexyl |
| H | 2-ethylcyclopentyl |
| $C_2H_5$ | 2-ethyl-4,5-dimethylcyclooctyl |
| i-$C_3H_7$ | $-H_2C-\overset{H}{\underset{|}{C}}=CH_2$ |

TABLE I-continued $$\underset{R}{\overset{R_3}{\underset{|}{NC-CHC}}}\overset{NH}{\underset{OR}{\diagup\!\!\!\diagdown}}$$

| R | R₃ |
|---|---|
| cyclopentyl | $H_2C=\overset{H}{\underset{|}{C}}-(CH_2)_3CH_2-$ |
| H | t-C₄H₉ |
| cyclopentyl | $-CH_2-$phenyl |
| cyclohexyl | $-\overset{CH_3}{\underset{\underset{CH_3}{|}}{\overset{|}{C}}}-$phenyl |
| | $-CH=CH_2$ |
| t-C₄H₉ | |
| C₆H₁₃ | $-CH_2-CH=\overset{CH_3}{\underset{|}{C}}-CH_3$ |
| | $-CH_2-(CH_2)_5-$phenyl |

Preferred R groups are alkyl of one to three carbon atoms, inclusive.

The R₃-substituted 2-cyanoacetimidate acid addition salt starting material is then reacted with cyanamide in an organic solvent to form the N,2-dicyanoacetimidate of the Formula IV. It is preferred that the solvent be essentially dry and inert to the reactants and products so as to maximize yield. Dryness is more preferred.

The acid addition salt can be present per se or can be made in situ by the addition of acid to the reaction vessel. Organic solvents, which can be employed are aromatics, halogenated lower alkanes, ethers, and alcohols. Illustrative examples of aromatics include benzene, toluene, xylenes and the like. Halogenated lower alkanes include methylene chloride, chloroform, dichloroethane, isopropyl chloride and the like. Ethers include cyclic and alicyclic ethers, such as diethyl ether, dipropyl ether, tetrahydrofuran, 1,4-dioxane and the like. Alcohols include methanol, ethanol, propanol, butanol and the like. Aromatic and halogenated lower alkanes are preferred.

The temperature of the reaction depends upon the solvent employed and the length of desired reaction time. Temperature is not an unduly significant parameter. Temperatures of from about 0° to about 100° C. can be employed with facility. Temperatures of from about 20° to about 40° C. are preferred.

The side product ammonium salts are preferably filtered from the reaction vessel. Although not necessary, a catalytic quantity of a molecular sieve can be employed. Suitable molecular sieves are powdered Linde 4A and other like catalysts.

The N,2-dicyanoacetimidate of Formula IV is then reacted with the amine

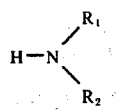

to form the desired R₃-substituted 3-(cyanoimino)propionitrile. The same temperature range and solvents used in the previous step can also be used in this nucleophilic substitution. Water may be added to the solvent system if desired. Halogenated lower alkanes such as methylene chloride, lower alcohols and cyclic ethers are preferred as solvents.

Following are examples of the invention process. These examples are intended to illustrate and not limit the inventive concept.

EXAMPLE 1

3-(Cyanoimino)-3-piperidinopropionitrile a. Ethyl 2-cyanoacetimidate hydrochloride HCl gas is bubbled vigorously through an ice cold solution of 33.0 g (0.50 m) malononitrile (Eastman, practical) and 23.0 g (0.50 m) dry ethanol in 400 ml of dry ether for 1.5 hour. The resultant precipitate is filtered, washed with ether, and dried at room temperature in vacuo to yield 72 g product (97%).

b. Ethyl N,2-dicyanoacetimidate

A mixture of 44.70 g (0.302 m) of ethyl 2-cyanoacetimidate hydrochloride and 13.29 g of cyanamide in 400 ml of benzene is stirred under nitrogen for 15 hours. The cyanamide is purified by ether extraction and concentration of the soluble portion in vacuo. After reaction, the precipitated ammonium chloride is filtered. The residue is washed twice with 50 ml benzene portions. The combined organic phases are concentrated in vacuo to give 41.36 g (100%) of a pale yellow crystalline material. The crystallization is exothermic. The product is very clean by tlc and nmr. The crude crystalline material melts at 51°–63° C.

nmr (CDCl₃): δ4.43 (2H, $q$, —OCH₂—), 3.93 (2H, $s$, CH₂), 1.38 (3H, $t$, CH₃).

c. 3-(Cyanoimino)-3-piperidinopropionitrile

Piperidine (25.67 g, 0.0302 m) is added dropwise to an ice-cooled solution of 41.36 g (0.0302 m) of ethyl N,2-dicyanoacetimidate in 60 ml of methanol. The reaction is heterogeneous initially, but soon becomes homogeneous and yellow. The piperidine is added at a rate that maintains a 25° C. reaction temperature. After 50 minutes, the reaction mixture is partitioned between CH₂Cl₂ and aqueous saturated NaHCO₃. The organic phase is dried over Na₂SO₄ and concentrated in vacuo to give 54 g of a yellow oil which by tlc appears to be pure product. Nmr confirms the presence of product.

EXAMPLE 2

3-(Cyanoimino)-3-morpholinopropionitrile

Morpholine (2.54 g, 0.0292 m) is added to an ice-cooled solution of 4.00 g (0.0292 m) of ethyl N,2-dicyanoacetimidate in 80 ml of tetrahydrofuran. After 145 minutes at room temperature, the reaction mixture is concentrated and filtered through 75 ml of silica gel. The silica gel is washed with 4% MeOH-CH₂Cl₂. The organic wash is concentrated. The resultant crude product is chromatographed (HPLC on 1 × 40 inches of 30–50 μ silica gel, 2% MeOH/CH₂Cl₂) to give product. This is crystallized from CH₂Cl₂/C₆H₁₂ to give 4.00 g of 1st crop white needles (129°–130°) and 0.350 g of 2nd crop (128°–130°), yield 84%. Nmr mass spec, and ir are consistent.

Analysis Calc'd for: $C_8H_{10}N_4O$: C, 53.92; H, 5.66; N, 31.44; Found: C, 53.77; H, 5.66; N, 31.23.

EXAMPLE 3

3-(Cyanoimino)-3-pyrrolidinopropionitrile

Pyrrolidine (2.07 g, 0.0292 m) is added to 4.00 g (0.0292 m) of an ice-cooled solution of ethyl N,2-dicyanoacetimidate in 80 ml of tetrahydrofuran and stirred for two hours at room temperature. The crude product is isolated and chromatographed in the same manner as that of Example 2. The tlc-pure crystalline product (4.80 g) is triturated with diethyl ether to give 4.00 g (84%), mp 45° C. Nmr and ir are consistent.

Analysis Calc'd for: $C_8H_{10}N_4$: C, 59.24; H, 6.21; N, 34.54; Found: C, 58.51; H, 6.33; N, 33.67.

EXAMPLE 4

3-(Cyanoimino)-3-(N,N-diethylamino)propionitrile

Diethylamine (4.27 g, 0.0584 m) is added to a solution of 8.00 g (0.0585 m) ethyl, N,2-dicyanoacetimidate in 80 ml of tetrahydrofuran. The mixture is stirred at room temperature for 6 hours and stored at 0° C. overnight. The reaction is concentrated and chromatographed (HPLC, 1 × 40 inches of 30–50 μ silica gel, 1% MeOH-$CH_2Cl_2$) to give 4.00 g product, 42%. The ir, nmr, and mass spec are consistent with the desired product.

EXAMPLE 5

3-(Cyanoimino)-3-(2-methylpiperidino)propionitrile

A solution of 4.00 g (0.0292 m) of ethyl N,2-dicyanoacetimidate and 2.86 g (0.0292 m) 2-methylpiperidine in 80 ml of tetrahydrofuran is stirred for 5 days at room temperature. The reaction product is isolated in the same way as 3-(cyanoimino)-3-(N,N-diethylamino)propionitrile to give 0.76 g of product, 14%. This product is further purified by chromatography on a Merck "B" column to give material whose nmr, ir, and mass spec are consistent with the desired product.

EXAMPLE 6

3-(Cyanoimino)-3-(N,N,dimethylamino)propionitrile

To an ice-cooled solution of 4.00 g (0.0292 m) of ethyl N,2-dicyanoacetimidate in 60 ml of tetrahydrofuran is added 5.27 g (0.0292 m) of a 25% solution of $Me_2NH$ in water. After stirring at room temperature for 1 hour, the reaction is concentrated and filtered through silica gel (2% MeOH/$CH_2Cl_2$ eluent). The organic phase is concentrated and chromatographed (HPLC, 1 × 40 inches of 30–50 μ silica gel, gradient $CHCl_3$ to 2% MeOH/$CHCl_3$). The resultant crystalline product (3.09 g, 78%) is triturated with ether to give 2.70 g, 61°–62° C. Nmr, ir and mass spec are consistent.

Analysis Calc'd for: $C_6H_8N_4$: C, 52.92; H, 5.92; N, 41.13; Found: C, 52.89; H, 6.06; N, 41.19.

EXAMPLE 7

3-(Cyanoimino)-3-(N,N-diallylamino)propionitrile

A solution of 4.00 g (0.0292 m) ethyl N,2-dicyanoacetimidate and 2.83 g (0.0292 m) diallylamine in 60 ml tetrahydrofuran is stirred at 0° C. for 12 hours. The reaction is concentrated and filtered through silica gel (2% MeOH/$CH_2Cl_2$ eluent). The organic phase is concentrated and the residue chromatographed (HPLC, 1 × 40 inches of 30–50 μ silica gel, 2% MeOH/$CH_2Cl_2$) to give product. A minor impurity (200 mg) crystallizes out from $CH_2Cl_2$-$C_6H_{12}$. The residual oil (3.08 g, 56%) has nmr, ir, and mass spec which are consistent.

EXAMPLE 8

The 3-(cyanoimino)-3-(amino)propionitriles of Examples 1–7 are converted to the corresponding 6-amino-2,4-diaminopyrimidine-3-oxide by treatment with hydroxylamine hydrochloride and potassium carbonate, as in Ser. No. 464,476.

EXAMPLE 9

In a manner similar to the process of Example 1, each of the following 2-cyanoacetimidate hydrochlorides

| R |
|---|
| methyl |
| propyl |
| isopropyl |
| butyl |
| 2-butyl |
| t-butyl |
| isoamyl |
| 2,2-dimethylbutyl |
| cyclopentyl |
| cyclohexyl |
| cycloheptyl | in reacted with cyanamide in an essentially dry inert organic solvent to form the corresponding N,2-dicyanoacetimidates of Formula IV.

EXAMPLE 10

In a manner similar to Examples 1–7, each of the N,2-dicyanoacetimidates of Example 9 are reacted with an amine

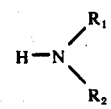

| $R_1$ | $R_2$ |
|---|---|
| methyl | ethyl |
| propyl | butyl |
| hexyl | octyl |
| isobutyl | methyl |
| heptyl | hydrogen |
| methyl | ethenyl |
| butyl | 2-propenyl |
| 3-heptenyl | 3-butenyl |
| pentyl | 2-isohexenyl |
| hydrogen | 4,4-dimethylcyclohexyl |
| cyclopentyl | hydrogen |
| hydrogen | hydrogen |
| methyl | n-butyl |
| 3-methylcyclopentyl | hydrogen |
| cyclohexyl | ethyl |
| 3,5-diethylcycloheptyl | hydrogen |
| hydrogen | cyclooctyl |
| cycloheptyl | 3-butenyl |
| 2-phenylbutyl | hydrogen |
| hydrogen | 3-phenylpentyl |
| methyl | 3-phenylbutyl |
| benzyl | benzyl |
| 2-phenylpentyl | hydrogen |
| 2-phenylethyl | cyclohexyl |
| 1-phenylpropyl | 2-isobutenyl |

| R₁ | R₂ |
|---|---|

H—N with R₁ and R₂ forming a ring:

azetidine
pyrrolidine
hexahydroazepine
heptamethylenimine
morpholine
piperazine
N-methylpiperazine
2-methylazetidine
3-ethylpyrrolidine
2,4-dimethylpiperidine
3-ethyl-5-propylhexahydroazepine
2-methyl-3-ethyl-5-isopropylheptamethylenimine
3-methylmorpholine
3,5-dipropylpiperazine
N,3-diethylpiperazine to form the respective 3-(cyanoimino)-3-(amino)propionitrile 3-(cyanoimino)-3-(N-methyl-N-ethylamino)propionitrile,
3-(cyanoimino)-3-(N-propyl-N-butylamino)propionitrile,
3-(cyanoimino)-3-(N-hexyl-N-octylamino)propionitrile,
3-(cyanoimino)-3-(N-isobutyl-N-methylamino)propionitrile,
3-(cyanoimino)-3-(N-heptylamino)propionitrile,
3-(cyanoimino)-3-(N-methyl-N-ethenylamino)propionitrile,
3-(cyanoimino)-3-(N-butyl-N-2-propenylamino)propionitrile,
3-(cyanoimino)-3-(N-3-heptenyl-N-3-butenylamino)propionitrile,
3-(cyanoimino)-3-(n-pentyl-N-2-isohexenylamino)propionitrile,
3-(cyanoimino)-3-(N-4,4-dimethylcyclohexylamino)propionitrile
3-(cyanoimino)-3-(N-cyclopentylamino)propionitrile,
3-(cyanoimino)-3-aminopropionitrile,
3-(cyanoimino)-3-(N-methyl-N-n-butylamino)propionitrile,
3-(cyanoimino)-3-(N-3-methylcyclopentylamino)propionitrile
3-(cyanoimino)-3-(N-cyclohexyl-N-ethylamino)propionitrile,
3-(cyanoimino)-3-(N-3,5-diethylcycloheptylamino)propionitrile,
3-(cyanoimino)-3-(N-cyclooctylamino)propionitrile,
3-(cyanoimino)-3-(N-cycloheptyl-N-3-butenylamino)propionitrile,
3-(cyanoimino)-3-(N-2-phenylbutylamino)propionitrile,
3-(cyanoimino)-3-(N-3-phenylpentylamino)propionitrile,
3-(cyanoimino)-3-(N-3-phenylbutyl-N-methylamino)propionitrile,
3-(cyanoimino)-3-(N,N-dibenzylamino)propionitrile,
3-(cyanoimino)-3-(N-2-phenylpentylamino)propionitrile,
3-(cyanoimino)-3-(N-cyclohexyl-N-2-phenylethylamino)propionitrile,
3-(cyanoimino)-3-(N-2-isobutenyl-N-1-phenylpropylamino)propionitrile,
3-(cyanoimino)-3-azetidinopropionitrile,
3-(cyanoimino)-3-pyrrolidinopropionitrile,
3-(cyanoimino)-3-hexahydroazepinopropionitrile,
3-(cyanoimino)-3-heptamethyleniminopropionitrile,
3-(cyanoimino)-3-morpholinopropionitrile,
3-(cyanoimino)-3-piperazinopropionitrile,
3-(cyanoimino)-3-N-methylpiperazinopropionitrile,
3-(cyanoimino)-3-(2-methylazetidino)propionitrile,
3-(cyanoimino)-3-(3-ethylpyrrolidino)propionitrile,
3-(cyanoimino)-3-(2,4-dimethylpiperidino)propionitrile,
3-(cyanoimino)-3-(3-ethyl-5-propylhexahydroazepino)propionitrile,
3-(cyanoimino)-3-(2-methyl-3-ethyl-5-isopropylheptamethylenimino)propionitrile,
3-(cyanoimino)-3-(3-methylmorpholino)propionitrile,
3-(cyanoimino)-3-(3,5-dipropylpiperazino)propionitrile,
3-(cyanoimino)-3-(N,3-diethylpiperazino)propionitrile,

EXAMPLE 11

In a manner similar to the process of Examples 1–7, each of the following $R_3$-substituted N,2-dicyanoacetimidates of Example 9

| $R_3$ |
|---|
| methyl |
| ethyl |
| ethenyl |
| propyl |
| isopropyl |
| butyl |
| 1-isobutenyl |
| t-butyl |
| pentyl |
| isoamyl |
| hexyl |
| 3-hexenyl |
| cyclopentyl |
| 3,4-diethylcyclopentyl |
| cyclohexyl |
| 2-methylcyclohexyl |
| 4,4-dimethylcyclohexyl |
| cycloheptyl |
| cyclooctyl |
| benzyl |
| phenylethyl |
| 2-phenylpropyl |
| 3-phenylisobutyl |
| 1-phenylpentyl |
| 3-phenylhexyl | is reacted with piperidine to form the respective 2-substituted-3-(cyanoimino)-3-piperidinopropionitrile 2-methyl-3-(cyanoimino)-3-piperidinopropionitrile,
2-ethyl-3-(cyanoimino)-3-piperidinopropionitrile,
2-ethenyl-3-(cyanoimino)-3-piperidinopropionitrile,
2-propyl-3-(cyanoimino)-3-piperidinopropionitrile,
2-isopropyl-3-cyanoimino)-3-piperidinopropionitrile,
2-butyl-3-(cyanoimino)-3-piperidinopropionitrile,
2-(1-isobutenyl)-3-(cyanoimino)-3-piperidinopropionitrile,
2-(t-butyl)-3-(cyanoimino)-3-piperidinopropionitrile,
2-pentyl-3-(cyanoimino)-3-piperidinopropionitrile,
2-isoamyl-3-(cyanoimino)-3-piperidinopropionitrile,
2-hexyl-3-(cyanoimino)-3-piperidinopropionitrile,
2-(3-hexenyl)-3-(cyanoimino)-3-piperidinopropionitrile,
2-cyclopentyl-3-(cyanoimino)-3-piperidinopropionitrile, 2-(3,4-diethylcyclopentyl)-3-(cyanoimino)-3-piperidinopropionitrile,
2-cyclohexyl-3-(cyanoimino)-3-piperidinopropionitrile,
2-(2-methylcyclohexyl)-3-(cyanoimino)-3-piperidinopropionitrile,
2-(4,4-dimethylcyclohexyl)-3-(cyanoimino)-3-piperidinopropionitrile,
2-cycloheptyl-3-(cyanoimino)-3-piperidinopropionitrile,
2-cyclooctyl-3-(cyanoimino)-3-piperidinopropionitrile,
2-benzyl-3-(cyanoimino)-3-piperidinopropionitrile,
2-phenylethyl-3-(cyanoimino)-3-piperidinopropionitrile,
2-(2-phenylpropyl)-3-(cyanoimino)-3-piperidinopropionitrile,
2-(3-phenylisobutyl)-3-(cyanoimino)-3-piperidinopropionitrile,
2-(1-phenylpentyl)-3-(cyanoimino)-3-piperidinopropionitrile,
2-(3-phenylhexyl)-3-(cyanoimino)-3-piperidinopropionitrile.

EXAMPLE 12

2-$R_3$-substituted N,2-dicyanoacetimidates, where $R_3$ is any $R_3$ substituent of Example 11, are reacted with any of the amines of Example 10 according to the processes of Example 11 to give the appropriate 2-substituted-3-(cyanoimino)-3-(amino)propionitrile. Illustrative examples of such preparations are the reaction of ethyl 2-propyl-N,2-dicyanoacetimidate with diethyl amine to give 2-propyl-3-(cyanoimino)-3-(N,N-diethylamino)propionitrile; butyl 2-cyclohexyl-N,2-dicyanoacetimidate with azetidine to give 2-cyclohexyl-3-(cyanoimino)-3-(N-azetidino)propionitrile; cyclohexyl benzyl-N,2-dicyanoacetimidate with cyclopentylamine to give 2-benzyl-3-(cyanoimino)-3-(N-cyclopentylamino)propionitrile.

It should be noted that the 2-$R_3$-substituted 3-(cyanoimino)-3-(amino)propionitriles of Examples 11 and 12 are named as the propionitriles even when the $R_3$ group is aliphatic. This is done to maintain internal consistency with the remainder of the specification and claims. The structure is clear from the name employed.

We claim:
1. A compound of the formula

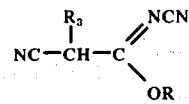

wherein

R is selected from the group consisting of alkyl of one to six carbon atoms, inclusive, and cycloalkyl of five to seven carbon atoms, inclusive;

$R_3$ is selected from the group consisting of hydrogen, alkyl of one to six carbon atoms, inclusive, alkenyl of two to six carbon atoms, inclusive, cycloalkyl of five to eight carbon atoms, substituted or unsubstituted with one to three alkyl groups, said alkyl group having from one to three carbon atoms, inclusive, alkyl being the same or different if two or three alkyl groups, and phenylalkyl wherein alkyl is from one to six carbon atoms, inclusive.

2. A compound in accordance with claim 1 wherein R is alkyl of one to three carbon atoms, inclusive, and $R_3$ is hydrogen or methyl.

3. A compound in accordance with claim 2 wherein $R_3$ is hydrogen.